(12) United States Patent
Pohjonen et al.

(10) Patent No.: US 11,272,882 B2
(45) Date of Patent: Mar. 15, 2022

(54) ELECTRODE FOR A USER WEARABLE APPARATUS

(71) Applicant: Nokia Technologies Oy, Espoo (FI)

(72) Inventors: Helena Pohjonen, Espoo (FI); Pekka Korpinen, Espoo (FI); Jarkko Rouvinen, Espoo (FI); Kim Blomqvist, Espoo (FI)

(73) Assignee: Nokia Technologies Oy, Espoo (FI)

( * ) Notice: Subject to any disclaimer, the term of this patent is extended or adjusted under 35 U.S.C. 154(b) by 360 days.

(21) Appl. No.: 15/565,517

(22) PCT Filed: Apr. 13, 2016

(86) PCT No.: PCT/FI2016/050240
§ 371 (c)(1),
(2) Date: Oct. 10, 2017

(87) PCT Pub. No.: WO2016/166414
PCT Pub. Date: Oct. 20, 2016

(65) Prior Publication Data
US 2018/0020975 A1 Jan. 25, 2018

(30) Foreign Application Priority Data
Apr. 17, 2015 (EP) .................................. 15163945

(51) Int. Cl.
*A61B 5/024* (2006.01)
*A61B 5/00* (2006.01)
(Continued)

(52) U.S. Cl.
CPC ............ *A61B 5/681* (2013.01); *A61B 5/0059* (2013.01); *A61B 5/02416* (2013.01);
(Continued)

(58) Field of Classification Search
CPC ...... A61B 5/02416–02433; A61B 5/026–0261
See application file for complete search history.

(56) References Cited

U.S. PATENT DOCUMENTS 5,387,122 A * 2/1995 Goldberger ........ A61B 5/02433
439/353
5,788,634 A * 8/1998 Suda .................. A61B 5/02416
600/372

(Continued)

FOREIGN PATENT DOCUMENTS

CN 1802140 7/2006
CN 104257367 1/2015
(Continued)

OTHER PUBLICATIONS

"Embrace—A Gorgeous Watch for you, Designed to Save Lives", Indiegogo, Retrieved on Sep. 12, 2017, Webpage available at: https://www.indiegogo.com/projects/embrace-a-gorgeous-watch-designed-to-save-lives.
(Continued)

*Primary Examiner* — Meredith Weare
(74) *Attorney, Agent, or Firm* — Locke Lord LLP

(57) ABSTRACT

An electrode for a user wearable apparatus; the electrode comprising: a conductive part comprising conductive material, wherein the conductive part is configured to provide electrical connection to electronic components of the user wearable device, and an opening configured to provide an optical connection to electronic components of the user wearable apparatus through the electrode.

15 Claims, 10 Drawing Sheets

(51) Int. Cl.
  *A61B 5/0531* (2021.01)
  *A61B 5/0533* (2021.01)
  *A61B 5/0535* (2021.01)
  *A61B 5/282* (2021.01)
  *A61B 5/1455* (2006.01)

(52) U.S. Cl.
  CPC ........ *A61B 5/02427* (2013.01); *A61B 5/0531* (2013.01); *A61B 5/0533* (2013.01); *A61B 5/0535* (2013.01); *A61B 5/282* (2021.01); *A61B 5/6831* (2013.01); *A61B 5/0095* (2013.01); *A61B 5/1455* (2013.01); *A61B 5/6824* (2013.01); *A61B 2562/0233* (2013.01); *A61B 2562/06* (2013.01); *A61B 2562/228* (2013.01)

(56) References Cited

U.S. PATENT DOCUMENTS

| | | | |
|---|---|---|---|
| 8,363,993 | B2 | 1/2013 | Yu et al. |
| 2004/0117212 | A1 | 6/2004 | Kong et al. |
| 2004/0133081 | A1* | 7/2004 | Teller ............... A61B 5/0022 600/300 |
| 2004/0173220 | A1 | 9/2004 | Harry et al. |
| 2010/0268056 | A1 | 10/2010 | Picard et al. |
| 2011/0245633 | A1 | 10/2011 | Goldberg et al. |
| 2014/0257053 | A1* | 9/2014 | Yuen ............... A61B 5/318 600/301 |
| 2014/0275845 | A1* | 9/2014 | Eagon ............... A61B 5/6826 600/301 |
| 2014/0275852 | A1* | 9/2014 | Hong ............... A61B 5/02427 600/301 |
| 2016/0070403 | A1* | 3/2016 | Sharma ............... A61B 5/6833 345/174 |
| 2016/0166153 | A1* | 6/2016 | Woo ............... A61B 5/14552 600/324 |

FOREIGN PATENT DOCUMENTS

| | | |
|---|---|---|
| WO | 2013/132147 A2 | 9/2013 |
| WO | 2014/088768 A2 | 6/2014 |

OTHER PUBLICATIONS

"Q Sensor Software", affectiva.com, Retrieved on Sep. 14, 2017, Webpage available at: http://qsensor-support.affectiva.com/.

"Fiber Coupled LEDs", Sensor Electronic Technology Inc(SETI), Retrieved on Sep. 12, 2017, Webpage available at: http://www.s-et.com/uvclean-sheets/fiber-coupled-leds.pdf.

"3mm Fiber RGB LED—Modules", DieMount GmbH, Retrieved on Sep. 12, 2017, Webpage available at: http://www.diemount.com/wp-content/uploads/2017/03/090127_SL_RGB-POF.pdf.

Poh et al., "A Wearable Sensor for Unobtrusive, Long-Term Assessment of Electrodermal Activity", IEEE Transactions on Biomedical Engineering, vol. 57, No. 5, May 2010, pp. 1243-1252.

Garbarino et al., "Empatica E3—A Wearable Wireless Multi-sensor Device for Real-Time Computerized Biofeedback and Data Acquisition", EAI 4th International Conference on Wireless Mobile Communication and Healthcare (Mobihealth), Nov. 3-5, 2014, 4 pages.

Extended European Search Report received for corresponding European Patent No. 15163945.7, dated Aug. 3, 2015, 7 pages.

International Search Report and Written Opinion received for corresponding Patent Cooperation Treaty Application No. PCT/FI2016/050240, dated Jun. 14, 2016, 11 pages.

English Language Machine Translation of Chinese Patent Application Publication No. CN104257367, published on Jan. 7, 2015, 28 pages.

Chinese Search Report for Chinese Patent Application No. 2016800215176 dated Dec. 21, 2019, 3 pages.

Examination Report of European Patent Application No. 15163945.7 dated Jul. 28, 2020, 5 pages.

European Examination Report dated Dec. 7, 2020 for European Patent Application No. 15163945.7, 6 pages.

Summons to attend oral proceedings pursuant to Rule 115(1) EPC dated Apr. 22, 2021 for corresponding European Patent Application No. 15 163 945.7-1113, 7 pages.

European Patent Office "Provision of a copy of the minutes in accordance with Rule 124(4) EPC" of the oral proceedings before the Examining Division dated Dec. 17, 2021 for European Patent Application No. 15163945.7, 17 pages.

* cited by examiner

ELECTRODE FOR A USER WEARABLE APPARATUS

RELATED APPLICATION

This application was originally filed as Patent Cooperation Treaty Application No. PCT/FI2016/050240 filed Apr. 13, 2016 which claims priority benefit to EP Patent Application 15163945.7 filed Apr. 17, 2015.

TECHNICAL FIELD

The present application generally relates to electrodes or components of user wearable (sensor) apparatuses.

BACKGROUND

This section illustrates useful background information without admission of any technique described herein representative of the state of the art.

Various metering devices that measure physiological conditions of users such as pulse sensors have become common for people to measure their own heart rate, movements or other parameters. The measurements can be performed using a chest strap that is worn under clothes or using a wrist worn watch-like sensor device.

Pulse or heart rate can be monitored for example optically using a photoplethymography (PPG) sensor. Also electrodermal activity (EDA) sensor can be used for measuring physiological conditions of the users.

SUMMARY

Various aspects of examples of the invention are set out in the claims.

According to a first example aspect of the present invention, there is provided an electrode for a user wearable apparatus; the electrode comprising:
 a conductive part comprising conductive material, wherein the conductive part is configured to provide electrical connection to electronic components of the user wearable device, and
 an opening configured to provide an optical connection to electronic components of the user wearable apparatus through the electrode.

In an embodiment, the conductive part of the electrode is configured to provide galvanic connection between a physiological condition sensor of the user wearable apparatus and a body of a user wearing the user wearable apparatus.

In an embodiment, the conductive part of the electrode is configured to provide electrical connection for charging the user wearable apparatus or for data transmission from/to the user wearable apparatus.

In an embodiment, the electrode comprises a light-passing element configured to provide the optical connection through the opening in the electrode. In an embodiment, the light-passing element comprises at least one of a light guide and a light fiber and a lens.

In an embodiment, the light-passing element comprises at least two optically separated light-passing elements. In an embodiment, one of the optically separated light-passing elements is operatively connected to a light source of an optical sensor of the user wearable apparatus and another one of the optically separated light-passing elements is operatively connected to a light detector of the optical sensor of the user wearable apparatus In an embodiment, the opening comprises a plurality of holes.

According to a second example aspect of the present invention, there is provided an electrode system comprising at least two electrodes disclosed in the foregoing. The at least two electrodes are configured to act as electrodes of a physiological condition sensor of the user wearable apparatus.

In an embodiment, the at least two electrodes comprise a first and a second electrode and wherein the first electrode is configured to provide an optical connection to a light source of an optical sensor of the user wearable apparatus and the second electrode is configured to provide an optical connection to a light detector of the optical sensor of the user wearable apparatus.

According to a third example aspect of the present invention, there is provided a user wearable apparatus comprising an electrode or an electrode system disclosed in the foregoing.

According to a third example aspect of the present invention, there is provided a method comprising:
 providing an electrode for a user wearable apparatus,
 providing in the electrode a conductive part comprising conductive material, wherein the conductive part is configured to provide electrical connection to electronic components of the user wearable device, and
 providing in the electrode an opening configured to provide an optical connection to electronic components of the user wearable apparatus through the electrode.

In an embodiment, the method further comprises: providing inside the electrode a light-passing element configured to provide the optical connection through the opening in the electrode.

In an embodiment, the method further comprises: providing the light-passing element by casting optical material into the electrode.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Example embodiments of the present invention and its potential advantages are understood by referring to FIGS. 1 through 12 of the drawings. In this document, like reference signs denote like parts or steps.

In various example embodiment of the invention there is provided a new type of an electrode or a contact element particularly suited for user wearable sensor devices.

In general terms there is provided an electrode that provides electrical connection for a first sensor type and optical connection for a second sensor type through the same electrode. The sensors herein are sensors that measure physiological conditions of a user and produce sensor signals corresponding to a property of the skin of the user or underlying matter (capillaries and veins, for example). The first sensor type may be any sensor type that utilizes electrical contact and the second sensor type may be any sensor type that utilizes optical contact.

In the following, various example embodiments are discussed in connection with optical heart rate sensors and electrodermal activity (EDA) sensors. Various embodiments are however not necessarily limited to these sensor types only. Instead the electrode of example embodiments can be used in monitoring some other physiological condition, too, and/or the electrode can be used for providing contact electrode for some other purpose. Electrical contact through the electrode can be used for charging and/or data transmission purposes for example.

Physiological conditions referred to herein may include one or more of the following: heart rate, blood pressure, skin/tissue moisture, sweating, skin/tissue conductance, skin/tissue resistance, skin/tissue impedance, impedance cardiogram, oxygen saturation level, glucose level, skin/tissue temperature. Also some other measurement type may apply.

Figure 1:
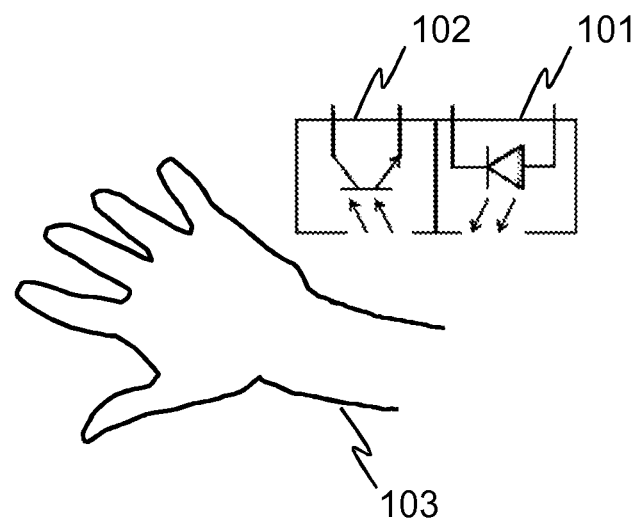
FIG. 1 is a simplified illustration of an example optical heart rate measurement.

Heart rate can be monitored optically by measuring variations in blood volume with a photoplethymography (PPG) sensor. FIG. 1 is a simplified illustration of an example optical heart rate measurement. FIG. 1 shows a (reflective type) PPG sensor that comprises a LED (light emitting diode) 101, a light source, and a photo diode (PD) 102, a light detector. The LED (optical emitter, light source) 101 emits light and the light detector 102 receives light rays reflected from a wrist 103 of a user.

Electrodermal activity refers to electrical changes measured at the surface of the skin of a user that arise when the skin receives innervating signals from the brain of the user. For most people experiencing emotional arousal, increased cognitive workload or physical exertion or something similar causes sweating. Our brains send signals to the skin to increase the level of sweating in such circumstances. One does not necessarily feel any sweat on the surface of the skin, but electrical conductance of the skin increases in a measurably significant way as the pores begin to fill below the surface of the skin.

Figure 2:
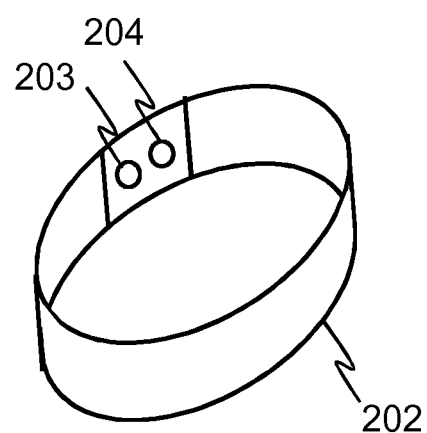
FIG. 2 is a simplified illustration of an example electrodermal activity sensor.

This electrical conductance of the skin can be measured by measuring e.g. impedance or resistance between two conductive electrodes. FIG. 2 is a simplified illustration of an example electrodermal activity, EDA, sensor. The EDA sensor is attached to a wrist strap 202 and two conductive electrodes 203 and 204 arranged on the inner surface of the strap so that the electrodes 203 and 204 become in contact with the skin of the user when the sensor is fitted around a wrist of the user.

An EDA sensor may alternatively use a four-point measurement, which needs four conductive electrodes for contacting the skin/surface. In such arrangement current is fed through two outer electrodes, and the skin/surface conductivity is measured between two inner electrodes. By using this method it is possible to eliminate contact resistances between the skin/surface and the electrode. These contact resistances can vary specifically in wearable devices.

In an embodiment, there is provided an electrode that is suited for both EDA measurement and optical sensor (e.g. PPG sensor). In other words, the same contact/electrode provides skin contact for EDA sensor and optical connection to the LED/PD of the optical sensor.

The electrodes provided in various embodiments of the invention may be used for ICG (Impedance Cardiogram) measurements, too. ICG measurement needs electrodes in contact with the skin the same way as EDA measurement.

FIGS. 3-6 show bottom view illustrations and cross sectional views of apparatuses 300 of various example embodiments.

The apparatus 300 comprises a body 301 and two contact elements/electrodes 310. The body 301 can be made of a suitable insulating material, such as for example plastic (e.g. acrylonitrile butadiene styrene (ABS) or polycarbonate (PC)), carbon fiber materials, glass, wood, ceramics or other material covered with fabric or leather or any combination of these.

The apparatus may be a user wearable apparatus that can be fitted around a body part (e.g. wrist or ankle) of a user using a strap (not shown). The strap may be made of suitable flexible or bendable material, such as plastic, fabric, and leather. In an example embodiment, the strap and the body 300 are integrally formed of one piece of material. The material can comprise or consist of any of the following: plastics, metals, nano-fibers, carbon fiber, leather, fabric and glass. The apparatus may be a device that is configured to be integrated into a garment of a user. The apparatus may be attached or integrated for example to a belt, a sock, a shoe, a sleeve or a collar of a shirt or pullover, and/or a waistband of trousers or skirt. The apparatus may be detachable from the garment. The apparatus 300 may be shaped like a watch and it may be configured to display time or other useful information to the user.

It is to be noted that the apparatus is fitted to be worn on the user so that the electrodes 310 have a contact to skin of the user wearing the apparatus.

The electrodes 310 comprise conductive parts 303 that comprise conductive material, e.g. metal, such as silver (Ag), gold (Au), copper (Cu) or aluminum (Al) etc. used. It may be beneficial to use an additional surface layer on top of the metal/conductive material, e.g. metallic silver with a silver chloride surface layer (Ag/AgCl). It may also be beneficial to choose a metal that does not cause allergies etc. since the electrode is intended for skin contact. It is to be noted that the electrode may comprise more than one conductive part or more than one piece of conductive material. The conductive parts comprised in one electrode are not necessarily electrically connected to each other. For example, the electrode may comprise a frame part made of e.g. plastic and the frame part may be covered/coated with conductive material. In an embodiment the frame part and/or the conductive part of the electrode forms walls that define outer dimensions of the electrode. The walls form a space inside the electrode.

The conductive part 303 comprises an opening 302 that allows light to pass through the electrode 310. The apparatus 300 comprises a printed wiring board, PWB, 305 (shown in the cross sectional view). Solder joints 306 attach the conductive parts 303 to the PWB 305. A light source 308 and a light detector 307 of an optical sensor are placed inside the electrode 310. This construction may provide thin structure and efficient utilization of PWB area.

Figure 3:
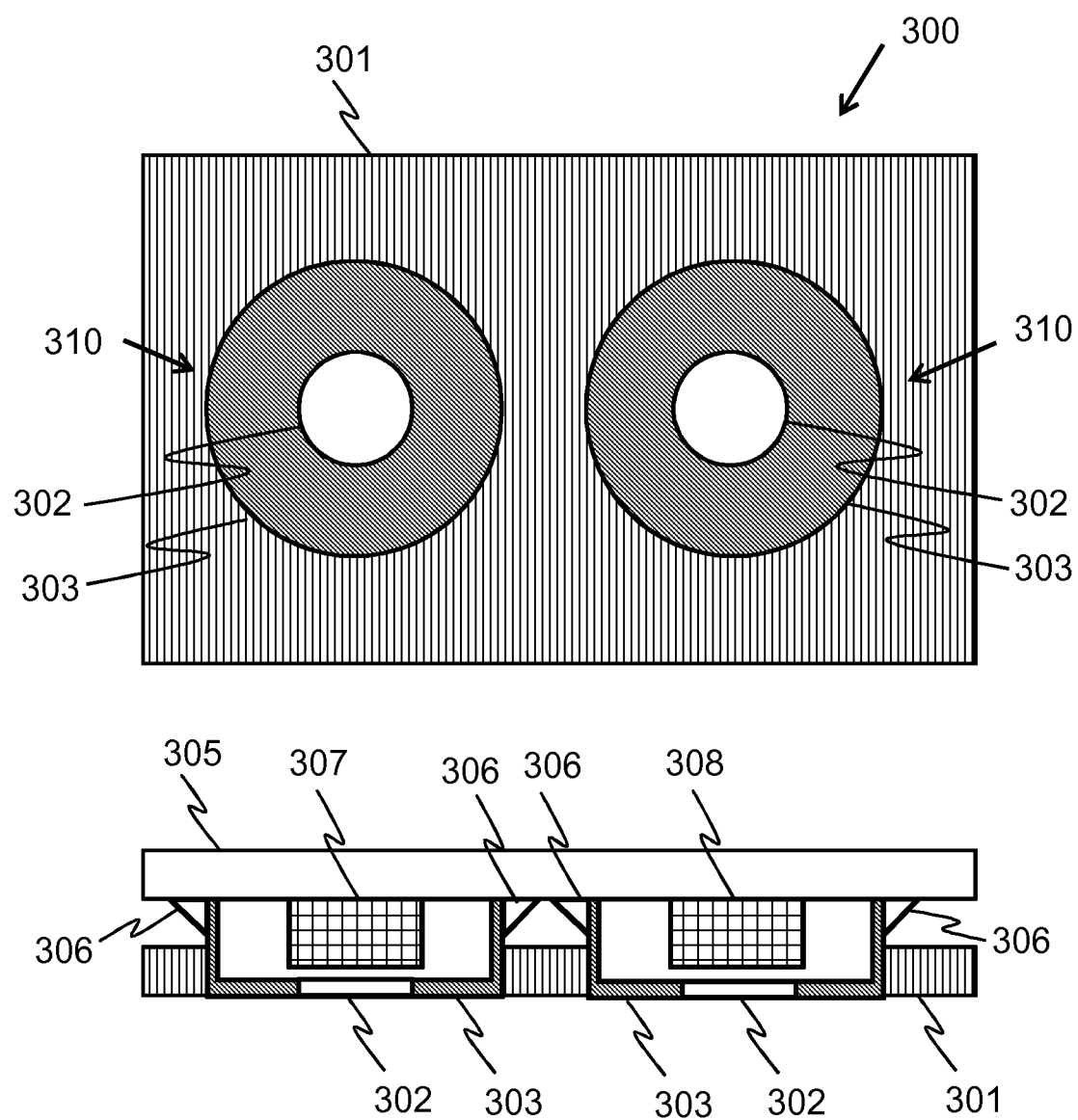
FIGS. 3-6 show bottom view illustrations and cross sectional views of apparatuses of various example embodiments.

In FIG. 3, the openings 302 that provide optical connection through the electrodes 310 may be covered with light-passing material such as glass.

Figure 4:
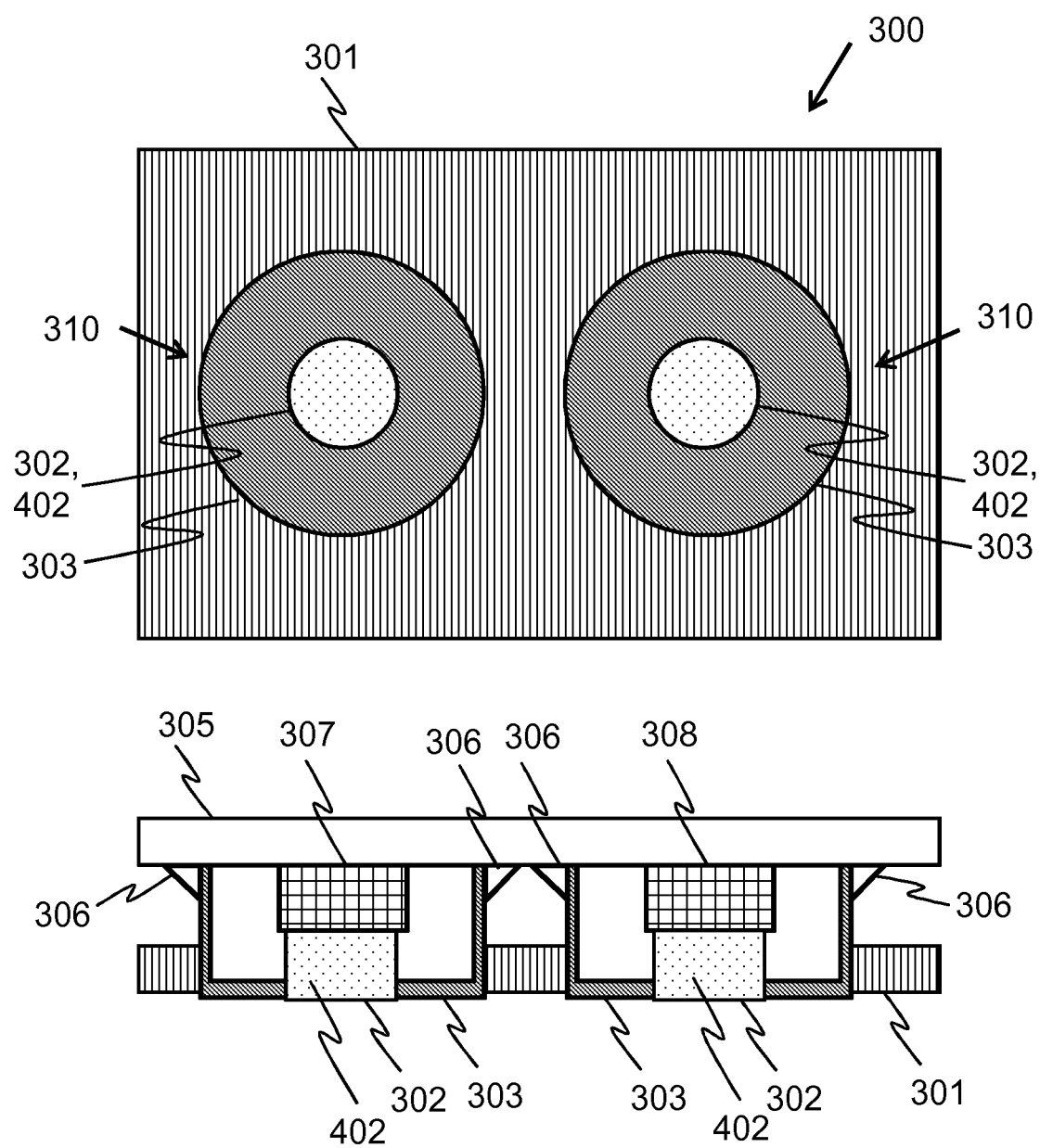

In the embodiment of FIG. 4, the apparatus comprises a light-passing element 402 inside the electrode 310. The light-passing element 402 may improve optical connection to and from the light detector 307 and the light source 308 through the opening 302 of the electrode 310. The light-passing element 402 extends from the opening 302 to the light source/detector. The light-passing element 402 may comprise for example a light guide, a light fiber, lenses, glass or some other optical component with suitable optical characteristics. Light guides and fibers are typically made of silicon dioxide (SiO2) or similar and do not cause allergies when undoped. Therefore light guides and fibers are suited for skin contact through the electrode 310.

Figure 5:
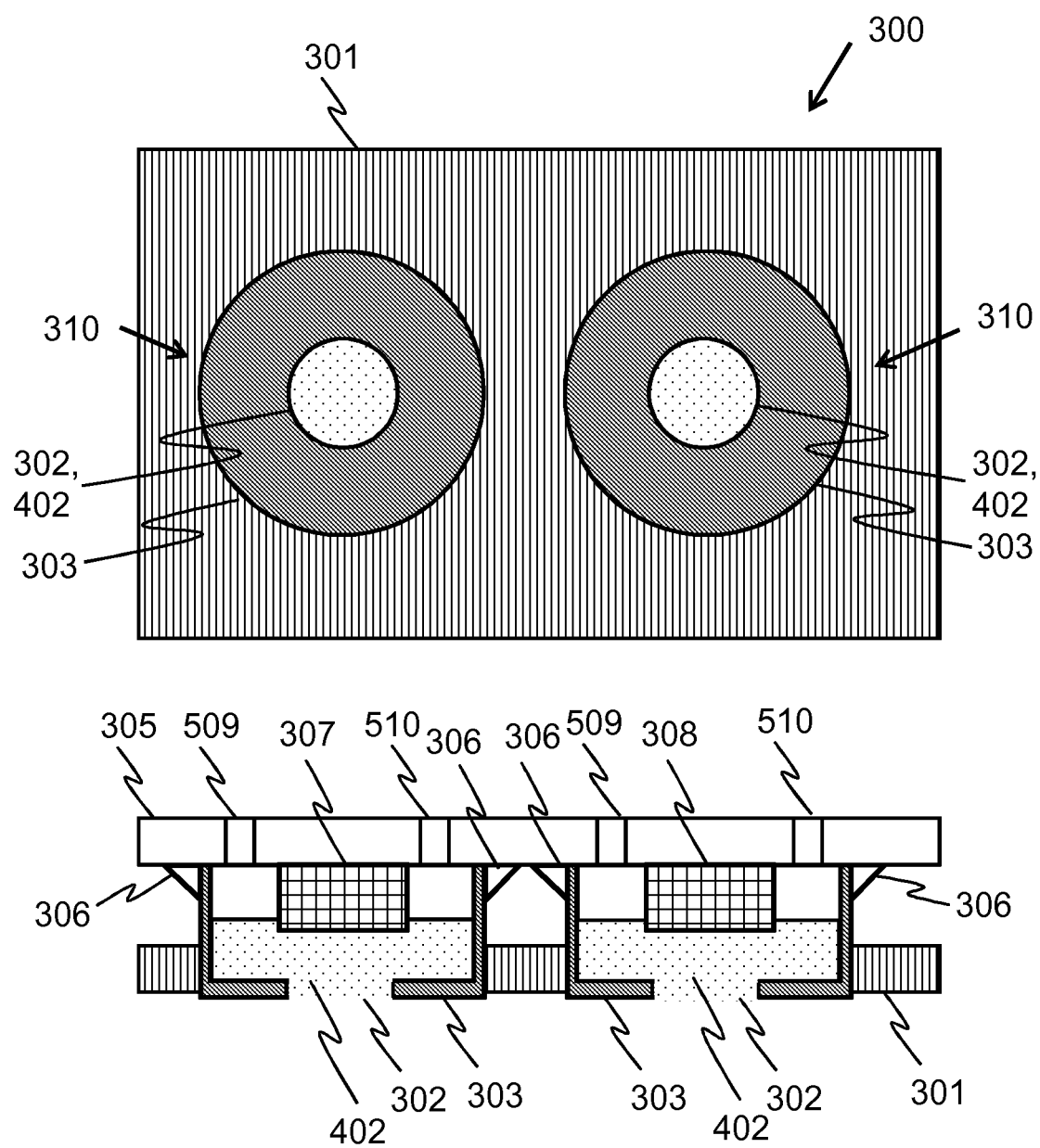

FIG. 5 shows an alternative implementation example obtained as a result of one potential method to manufacture the light-passing element 402 into the electrode 310. In the shown example, the light-passing element 402 has been casted into the electrode 310. First, the outer surface of the electrode 310 is placed into a tool (not shown in the picture), which blocks the opening 302 of the electrode 310 and creates a suitable outer surface for the light-passing element 402. The PWB 305 comprises openings 509 and 510 that provide access to the inner side of the electrode 310. Suitable optical material (e.g. Epoxy resin) is poured into the electrode 310 from the PWB side through the openings 510. The other openings 509 allow air to exit the mold formed by the electrode 310 as the optical material is poured into the mold. The apparatus is removed from the tool after the casted optical material is hardened.

A technical effect of the manufacturing method and/or resulting apparatus structure is that there is no air gap between the optical element 402 and the sensor elements 307 and 308 and optimal optical contact to the sensor elements 307 and 308 may be achieved. Another technical effect is that the optical element 402 provides protection for the sensor elements 307 and 308. Still other technical effects are that height of the setup may be decreased and simple and easy to use manufacturing process and tools may be used.

Figure 6:
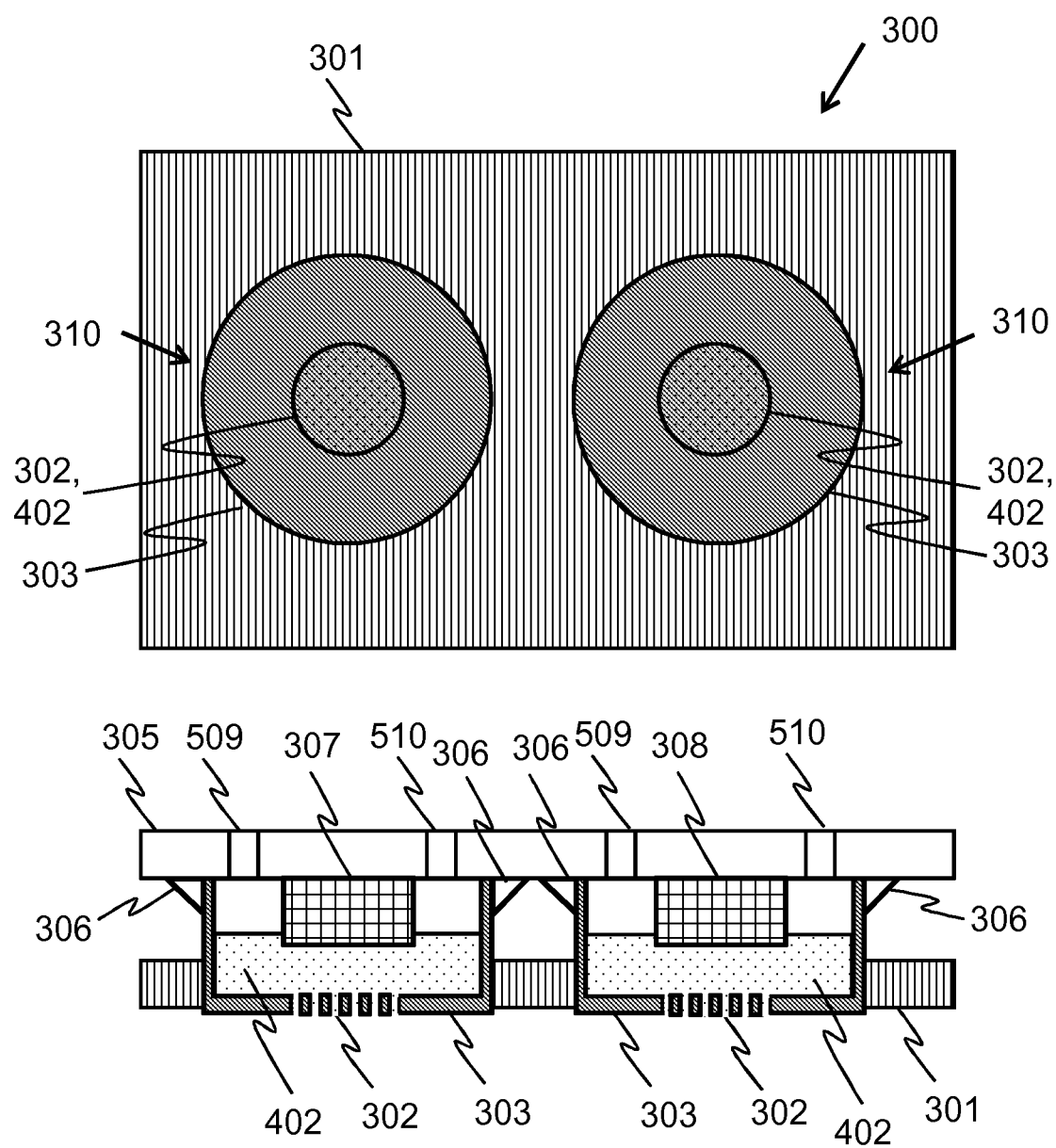

FIG. 6 shows an example embodiment where the opening 302 in the electrode 310 comprises a plurality of holes; a so called micro perforation is used instead of one larger opening. That is, there are many small holes 302 instead of one larger opening in the electrode 310. Diameter of the holes may be for example about 0.1 mm and may alternatively vary for example between 0.05-1.00 mm. In the shown example, the light-passing element 402 has been manufactured in the same way as in FIG. 5. A technical effect of the structure shown in FIG. 6 is that visual appearance of the apparatus may be improved as the micro perforation is almost invisible when the light of the light source 308 is not on.

It is to be noted that FIGS. 3-6 show the light source 308 and the light detector 307 of the optical sensor inside the electrode 310. Also other alternatives are possible. For example, the light source and the light detector of the optical sensor may be placed outside the electrode while a light-passing element, e.g. light fiber, is arranged to provide the optical connection to and from the light detector and the light source through the opening 302 in the electrode 310.

Further it is to be noted that even though FIGS. 3-6 show the conductive part 303 soldered to the PWB 305, also other alternatives are possible. It is not mandatory that the conductive part is attached to the PWB. Instead for example a floating or a suspended solution is possible as long as connection to the PWB and other components is provided in any suitable manner.

Figure 7:
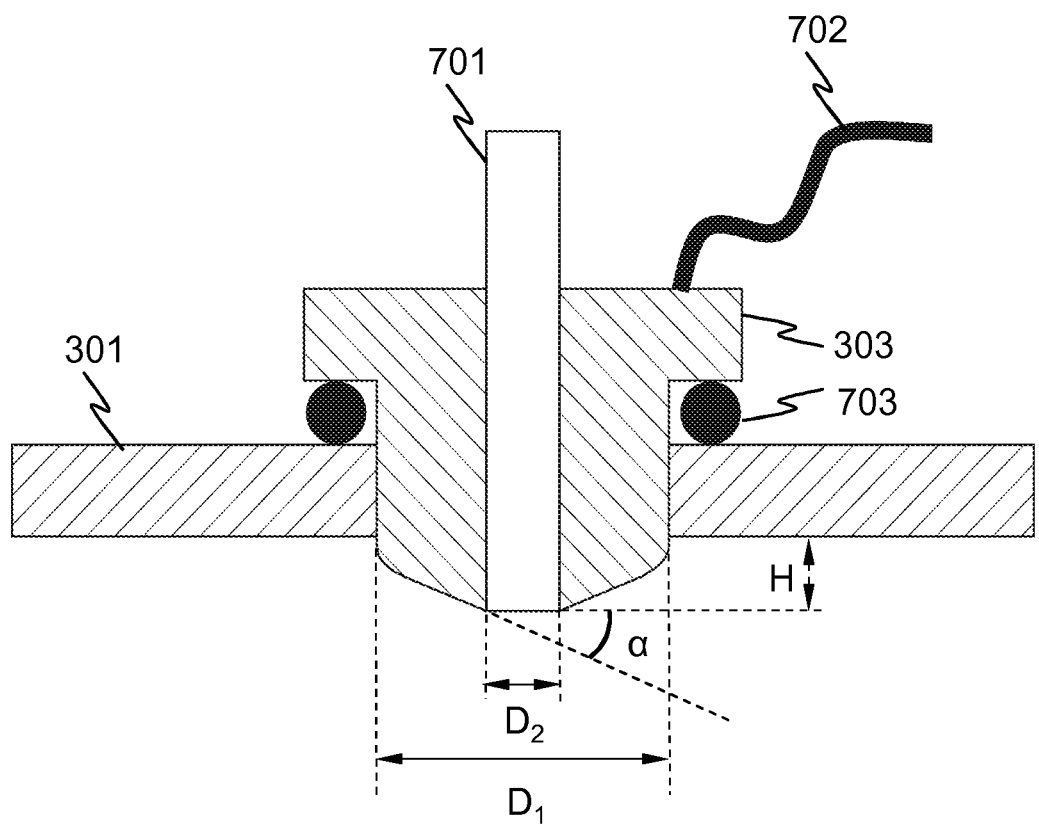
FIGS. 7-9 show cross sections of electrodes of various example embodiments.
Figure 8:
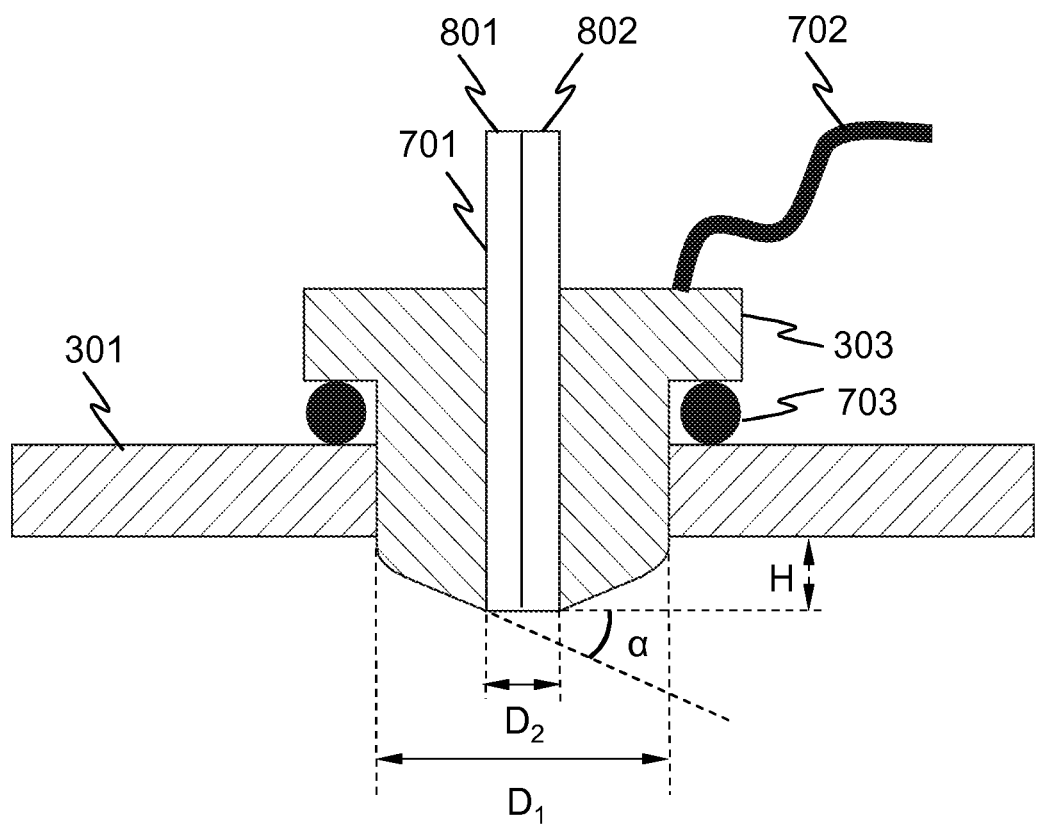
Figure 9:
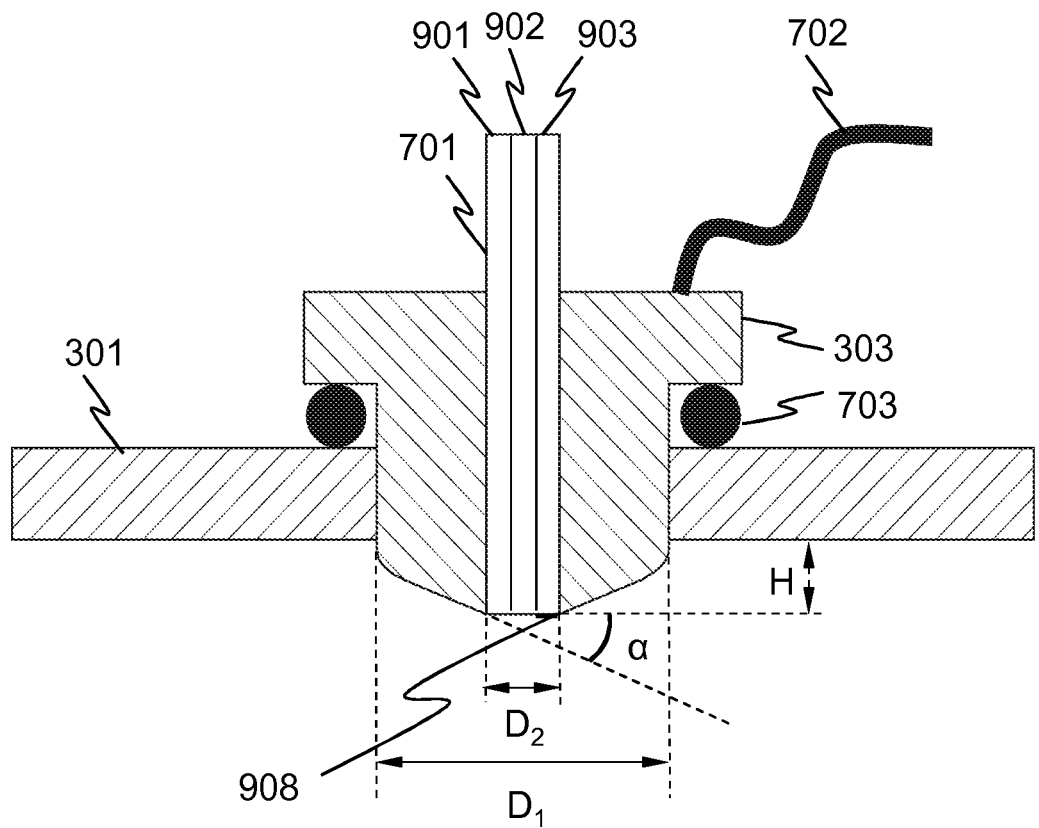

FIGS. 7-9 show cross sections of electrodes of various example embodiments. FIGS. 7-9 show a body 301 and conductive part 303 of the electrodes. The body 301 can be made of a suitable insulating material and the conductive part 303 is made of conductive material similarly as explained in connection with FIGS. 3-6.

A gasket 703, such as an o-ring, is provided between the conductive part 303 and the apparatus body or cover 301. The conductive part 303 comprises an opening 701 that allows optical connection through the conductive part 303 and the electrode. Electrical contact 702 provides electrical connection from the conductive part 303 to other components (electrical components of a user wearable apparatus).

In the shown example embodiments, a diameter of the conductive part 303 is D1 and a diameter of the opening 702 is D2. Protrusion height H (distance between the apparatus body surface and the highest point of the conductive part in relation to the apparatus body surface) and angle α define a visible form of the conductive part and the electrode. It is possible to choose values for D1, D2, H and α as desired. For example if α and H are 0, the electrode does not protrude at all from the apparatus body. In general it is noted that the physical dimensions of the electrode may be varied as desired. The electrode may for example form a round protrusion in the apparatus body or the electrode may be completely flat. The surface of the electrode may comprise wave like form or the surface may be smooth.

In FIG. 7, the opening 701 provides as such an optical connection through the conductive part 303. Alternatively the opening 701 may be filled with a light-passing element such as light fiber, light guide, lenses or other optical material to provide the optical connection through the conductive part 303.

In FIG. 8, the opening 701 comprises two optically separated light-passing elements 801 and 802, e.g. two light guides or light fibers. In an embodiment light fiber 801 is operatively/functionally connected to a light source element of an optical sensor and the light fiber 802 is operatively/functionally connected to a light detector element of an optical sensor. In an embodiment it may be possible to use the same electrode both for emitting and detecting light for the purposes of optical sensor. In an alternative embodiment only light source is activated in one electrode and only light detector is activated in another electrode.

FIG. 9 shows an embodiment where there are additional light-passing elements integrated into the conductive part 303 of the electrode. In the shown example the opening 701 comprises three optically separated light-passing elements 901-903, e.g. three light guides or light fibers. Such embodiment enables additional optical measurements. For example temperature of the skin may be measured using one of the optical connections 903 through the opening 701. In an embodiment, temperature is measured using pulsed light and detecting it's time to reflect from the end of the light fiber 903. In order to provide the reflection there may be a metal (e.g. gold (Au) or platinum (Pt)) coating 908 in the end of the light fiber 903. By using the pulsed temperature measurement through the same opening (parallel light fiber) it may be possible to compensate for self-heating effects of the light source of the optical sensor, because the measurement is based on the change of the length of the light fiber vs. temperature. In general, electrical measurements are temperature dependent. If temperature (e.g. in Kelvin) is measured and there's a model how the measurement works at different temperatures then the measurement can be compensated using the model. For example, accurate SpO2 measurement may need a temperature compensation to get correct reading in different temperatures. Now if the LED self-heats the electrode and thus the skin/tissue, the temperature change can be taken into account by optically measuring the fiber length, which may be related to the temperature. So here the travel time of light gives the length of the fiber and that length can be changed into Kelvins.

In an embodiment light fiber 901 is operatively/functionally connected to a light source element of an optical sensor, the light fiber 902 is operatively/functionally connected to a light detector element of an optical sensor, and the light fiber 903 is operatively/functionally connected to light source and detector of pulsed measurement.

Figure 10:
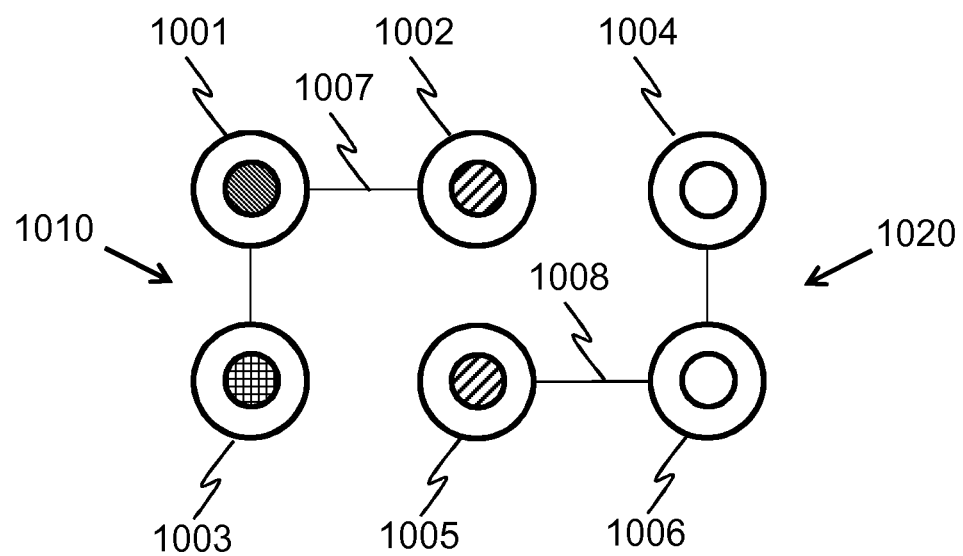
FIG. 10 shows an example arrangement with a plurality of electrodes.

In the foregoing, FIGS. 3-6 show examples with two electrodes. In those examples, there may be for example a green LED (light source) placed in to one of the electrodes and a light detector placed in to the other electrode for a PPG measurement. Concurrently these two electrodes may operate as contact electrodes for an EDA measurement. Also more than two electrodes can be used. FIG. 10 shows an example arrangement 1020 with a plurality of electrodes. The arrangement 1020 comprises six electrodes 1001-1006. Electrodes 1001-1003 are electrically connected together through electrical connections 1007 to form a first electrode for an EDA measurement and electrodes 1004-1006 are electrically connected together through electrical connections 1008 to form a second electrode for the EDA measurement. In this way an increased electrode contact area may be achieved. For the purposes of an optical sensor measurement different wavelengths are fed through different electrodes 1001-1006. In the shown example, the electrode 1001 is connected to a LED that emits red light, the electrode 1003 is connected to a LED that emits infrared light, and the electrodes 1002 and 1005 are connected to LEDs that emit green light. The electrodes 1004 and 1006 are connected to light detectors. In this way a multiwavelength sensor is provided.

Figure 11:
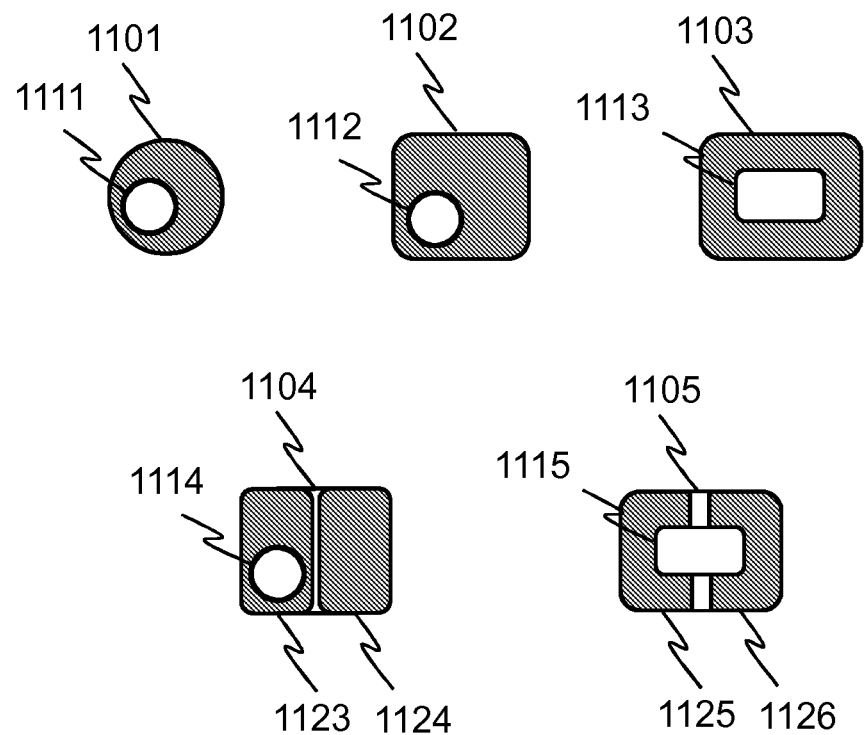
FIG. 11 shows top views of electrodes of various example embodiments.

In the foregoing examples the electrodes have a round form and the opening for the optical connection is placed in the middle of the electrode. It is not mandatory to use round shape or to place the opening for the optical connection in the middle of the electrode, though. Other shapes can be used. FIG. 11 shows top views of electrodes 1101-1105 of various example embodiments. An electrode 1101 has round shape with an opening 1111 for the optical connection placed near an edge of the electrode. An electrode 1102 has square like shape with a round opening 1112 for the optical connection placed near a corner of the electrode. An electrode 1103 has rectangular like shape with a rectangular like opening 1113 for the optical connection placed in the middle of the electrode.

An electrode 1104 has a square like shape with a round opening 1114 for the optical connection. The electrode 1104 comprises two conductive parts 1123 and 1124. The opening 1114 is placed near a corner of the electrode in an electrode area covered by the conductive part 1123. An electrode 1105 has rectangular like shape with a rectangular like opening 1113 for the optical connection placed in the middle of the electrode. The electrode 1105 comprises two conductive parts 1125 and 1126. It is noted that the multiple conductive parts e.g. in electrodes 1104 and 1105 may be electrically connected to each other, but this is not mandatory. In an embodiment the separate conductive parts of the electrode may be used for different purposes. In an embodiment, the separate conductive part of one electrode might for example form electrodes of an EDA sensor. It is noted that also other shapes and forms are possible.

Figure 12:
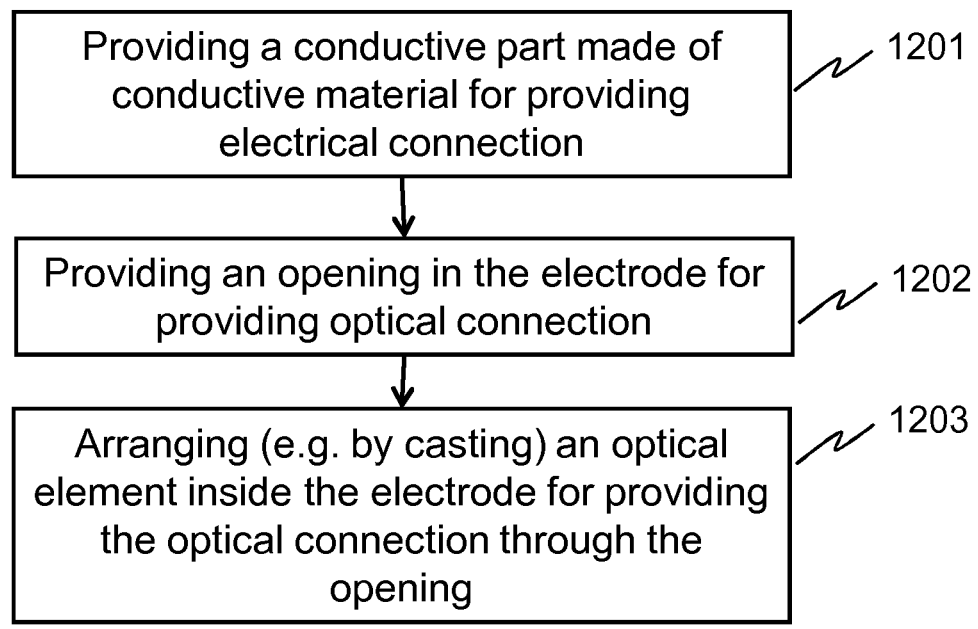
FIG. 12 shows a flow chart of a process of an example embodiment.

FIG. 12 shows a flow chart of a process of manufacturing an electrode of an example embodiment. The process comprises:

1201: Providing a conductive part made of conductive material for providing electrical connection to electronics of a user wearable apparatus. Electrical connection is provided for example to a first type of a physiological condition sensor or for charging purposes or for data communication purposes. The first type of a physiological condition sensor may be for example an EDA sensor or an ICG sensor or some other sensor utilizing electrical connection.

1202: Providing an opening in the electrode for providing optical connection to electronics of the user wearable apparatus. Optical connection is provided for example to a second type of a physiological condition sensor. The second type of a physiological condition sensor is an optical sensor and may be for example a PPG sensor or a temperature sensor.

1203: Arranging an optical element inside the electrode for providing the optical connection through the opening. The optical element is any suitable light-passing element, such as a light fiber, light guide, a lens or other optical material. It is to be noted that the optical element is not mandatory. Instead the opening in the electrode may suffice for providing the optical coupling. In an embodiment the optical element is manufactured by casting optical material into the electrode.

Without in any way limiting the scope, interpretation, or application of the claims appearing below, a technical effect of one or more of the example embodiments disclosed herein is that a new type of contact element or electrode is provided. Another technical effect of one or more of the example embodiments disclosed herein is that total device area needed for physiological sensors or electrodes thereof may be reduced. Device surface area needed for physiological measurements may be reduced as one electrode may be used for multiple purposes (e.g. different measurements, charging the device, and data transmission). In this way the number of possible measurement types in one device may be maximized.

Another technical effect of one or more of the example embodiments disclosed herein is that need for holes in device casing is minimized. Since same contact/electrode can be used for many purposes, a separate opening in the device cover is not needed for each sensor/electrode type. Another technical effect of one or more of the example embodiments disclosed herein is that no additional windows are needed in device casing. Thereby additional reflections due to windows when detecting the light are reduced. Another technical effect of one or more of the example embodiments disclosed herein is that internal light pollution (ILP) may be reduced as the electrode walls function as a light barrier between the light source and the light detector.

Another technical effect of one or more of the example embodiments disclosed herein is that when the electrode forms a small bump or protrusion. Therefore it may be that scattered light (e.g. ambient light) is minimized during the reflected light measurement as the electrode slightly penetrates into the skin/tissue of the user. Bump like structure may also improve SNR (signal to noise ratio) in PPG measurement. This is useful specifically in wearable devices when person wearing the device is running for example during the measurement.

Another technical effect of one or more of the example embodiments disclosed herein is that more flexibility in sensor designing. For example integrating the optical connection to EDA electrodes gives more freedom to place EDA and PPG measurement arrangements in the product. Another technical effect of one or more of the example embodiments disclosed herein is that the arrangement of electrodes may allow transmissive PPG measurements.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications, which may be made without departing from the scope of the present invention as defined in the appended claims.

The invention claimed is:

1. An electrode system for a user wearable apparatus, the electrode system comprising:
   at least two electrodes, wherein the at least two electrodes comprise a first electrode and a second electrode, wherein each of the first and the second electrodes are electrically isolated from one another on a same side of the user wearable apparatus and includes a conductive part comprising conductive material, wherein the conductive part is configured to provide electrical connection to electronic components of the user wearable device and is configured to provide electrical connection from a surface of the conductive part to a surface of skin of a body part of a user of the user wearable apparatus;
   an opening in the conductive part of at least the first electrode configured to provide an optical connection to the surface of the skin of the body part of the user;
   at least two optically separated light-passing elements in the opening in the conductive part of at least the first electrode, wherein the at least two light-passing elements comprise a first light-passing element and a second light-passing element;
   wherein the first light-passing element is connected to a first light source of a first optical sensor and is configured to pass light from the light source, through the opening in the conductive part of at least the first electrode, to the surface of the skin of the body part of the user, and to reflect the light as reflected light off the surface of the skin;
   wherein the second light-passing element is connected to a first light detector of the first optical sensor and is configured to pass the reflected light from the surface of the skin of the body part of the user, through the opening in the conductive part of at least the first electrode, to the light detector;
   a third light-passing element optically separated from the first and second light-passing elements in the opening in the conductive part of at least the first electrode, the third light-passing element including a reflecting surface in the end thereof;
   wherein the third light-passing element is connected to a second light source of a second optical sensor and is configured to pass light from the second light source, through the opening in the conductive part of at least the first electrode, to the reflecting surface in the end thereof, and to reflect the light as reflected light off the reflecting surface; and
   wherein the third light-passing element is connected to a second light detector of the second optical sensor and is configured to pass the reflected light from the reflecting surface in the end thereof, through the opening in the conductive part of at least the first electrode, to the second light detector.

2. The electrode system according to claim 1, wherein the conductive part of each of the first and second electrodes is configured to provide galvanic connection between a physiological condition sensor of the user wearable apparatus and a body of a user wearing the user wearable apparatus.

3. The electrode system according to claim 1, wherein the conductive part of each of the first and second electrodes is configured to provide electrical connection for charging the user wearable apparatus or for data transmission from/to the user wearable apparatus.

4. The electrode system according to claim 1, wherein at least one of the first, second, or third light-passing element comprises at least one of a light guide or a light fiber.

5. The electrode system according to claim 1, wherein at least one of the first, second, or third light-passing element comprises a lens.

6. The electrode system according to claim 1, wherein the first and second electrodes are configured to act as electrodes of a physiological condition sensor of the user wearable apparatus.

7. The electrode system according to claim 1, wherein the opening comprises a multitude of holes and each of the holes has a diameter of 0.1 mm.

8. The electrode system according to claim 1, wherein the opening comprises a multitude of holes and each of the holes has a diameter between 0.05 mm and 1.0 mm.

9. The electrode system according to claim 1, wherein a measurable temperature of the surface of the skin of the body part of the user is measured using pulsed light from the second light source and detecting with the second light detector a length of time to detect the reflected light from the reflecting surface in the end of the third light-passing element.

10. The electrode system according to claim 1, wherein the reflecting surface in the end of the third light-passing element is a metal coating of at least one of gold (Au) or platinum (Pt).

11. A user wearable apparatus comprising the electrode system according to claim 1.

12. A method comprising:
   providing an electrode system for a user wearable apparatus, the electrode system comprising at least two electrodes, wherein the at least two electrodes comprise a first electrode and a second electrode that are electrically isolated from one another on a same side of the user wearable apparatus, and include in each of the first and second electrodes a conductive part comprising conductive material, wherein the conductive part is configured to provide electrical connection to electronic components of the user wearable device and is configured to provide electrical connection from a surface of the conductive part to a surface of skin of a body part of a user of the user wearable apparatus;

providing an opening in the conductive part of at least the first electrode configured to provide an optical connection to the surface of the skin of the body part of the user;

providing at least two optically separated light-passing elements in the opening in the conductive part of at least the first electrode, wherein the at least two light-passing elements comprise a first light-passing element and a second light-passing element;

wherein the first light-passing element is connected to a first light source of an first optical sensor and is configured to pass light from the light source, through the opening in the conductive part of at least the first electrode, to the surface of the skin of the body part of the user, and to reflect the light as reflected light off the surface of the skin;

wherein the second light-passing element is connected to a first light detector of the first optical sensor and is configured to pass the reflected light from the surface of the skin of the body part of the user, through the opening in the conductive part of at least the first electrode, to the light detector;

a third light-passing element optically separated from the first and second light-passing elements in the opening in the conductive part of at least the first electrode, the third light-passing element including a reflecting surface in the end thereof;

wherein the third light-passing element is connected to a second light source of a second optical sensor and is configured to pass light from the second light source, through the opening in the conductive part of at least the first electrode, to the reflecting surface in the end thereof, and to reflect the light as reflected light off the reflecting surface; and wherein the third light-passing element is connected to a second light detector of the second optical sensor and is configured to pass the reflected light from the reflecting surface in the end thereof, through the opening in the conductive part of at least the first electrode, to the second light detector.

13. The method according to claim 12, wherein providing at least one of the first, second or third light-passing elements located in the first electrode is performed by casting optical material into the first electrode.

14. The method according to claim 12, wherein a measurable temperature of the surface of the skin of the body part of the user is measured using pulsed light from the second light source and detecting with the second light detector a length of time to detect the reflected light from the reflecting surface in the end of the third light-passing element.

15. The method according to claim 12, wherein the reflecting surface in the end of the third light-passing element is a metal coating of at least one of gold (Au) or platinum (Pt).

* * * * *